(12) United States Patent
Math et al.

(10) Patent No.: US 10,583,133 B2
(45) Date of Patent: Mar. 10, 2020

(54) PHARMACEUTICAL COMPOSITIONS OF LENVATINIB

(71) Applicant: SHILPA MEDICARE LIMITED, Raichur (IN)

(72) Inventors: Nijaguni Revansiddayya Rudraswamy Math, Vizianagaram (IN); Sreenivas Reddy, Vizianagaram (IN); Ravi Vamsi Peri, Vizianagaram (IN); Krishnamurthy Toppaladoddi, Vizianagaram (IN); Shivakumar Pradeep, Vizianagaram (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 0 days.

(21) Appl. No.: 16/289,677

(22) Filed: Mar. 1, 2019

(65) Prior Publication Data
US 2019/0275026 A1 Sep. 12, 2019

(30) Foreign Application Priority Data
Mar. 12, 2018 (IN) .............................. 201841009022

(51) Int. Cl.
A61K 31/47 (2006.01)
A61K 47/26 (2006.01)
A61K 47/38 (2006.01)
A61K 47/02 (2006.01)

(52) U.S. Cl.
CPC .............. *A61K 31/47* (2013.01); *A61K 47/02* (2013.01); *A61K 47/26* (2013.01); *A61K 47/38* (2013.01)

(58) Field of Classification Search
CPC ...................................................... A61K 31/47
USPC ......................................................... 514/312
See application file for complete search history.

(56) References Cited

U.S. PATENT DOCUMENTS

| | | |
|---|---|---|
| 7,253,286 B2 | 8/2007 | Funahashi et al. |
| 9,504,746 B2 | 11/2016 | Furitsu et al. |
| 2013/0296365 A1 | 11/2013 | Bando |

FOREIGN PATENT DOCUMENTS

| | | |
|---|---|---|
| WO | 2017028660 A1 | 2/2017 |
| WO | 2018185175 A1 | 10/2018 |

*Primary Examiner* — Kevin E Weddington (57) ABSTRACT

The present invention relates to a pharmaceutical composition comprising lenvatinib mesylate and a stabilizer in an amount of about 10% to about 20% based on the total weight of the composition, wherein the stabilizer is selected from the group consisting of calcium hydroxide and potassium hydroxide; and its process for preparation thereof.

9 Claims, 2 Drawing Sheets

PHARMACEUTICAL COMPOSITIONS OF LENVATINIB

FIELD OF THE INVENTION

The present invention relates to pharmaceutical composition comprising lenvatinib mesylate and a stabilizer selected from the group consisting of calcium hydroxide and potassium hydroxide; and the process for preparation thereof.

BACKGROUND OF THE INVENTION

E7080 (also known as lenvatinib mesylate) is an active inhibitor of multiple receptor tyrosine kinases (e.g., receptor tyrosine kinases involved in angiogenesis and tumor proliferation) including vascular endothelial growth factor (VEGF), fibroblast growth factor (FGF), platelet-derived growth factor receptor a (PDGFRα), KIT, and RET proto-oncogene receptors. Lenvatinib mesylate is structurally represented as:

The drug with the name lenvatinib, which contains lenvatinib mesylate, has been approved by the Food and Drug Administration (FDA) for the treatment of locally recurrent or metastatic, progressive thyroid cancer, resistant to radioactive iodine and for the treatment of advanced renal carcinoma.

U.S. Pat. No. 7,253,286 discloses the lenvatinib and its pharmaceutically acceptable salts such as hydrochloric acid salts, sulfuric acid salts, carbonic acid salts, bicarbonate salts, hydrobromic acid salts and hydroiodic acid salts; organic carboxylic acid addition salts such as acetic acid salts, maleic acid salts, lactic acid salts, tartaric acid salts, trifluoroacetic acid salts, methanesulfonic acid salts, hydroxymethanesulfonic acid salts, hydroxyethanesulfonic acid salts, benzenesulfonic acid salts, toluenesulfonic acid salts, taurine salts, trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts, phenethylbenzylamine salts, arginine salts, lysine salts, serine salts, glycine salts, aspartic acid salts and glutamic acid salts.

Lenvatinib mesylate degrades under humidifying and warm storage conditions when formulated into a pharmaceutical composition. Furthermore, it is known that lenvatinib mesylate forms gelation on the surface of pharmaceutical compositions, so that when the pharmaceutical compositions are stored under humidified conditions, delayed dissolution of the active ingredients may occur due to moisture absorption. U.S. Pat. No. 9,504,746 discloses a pharmaceutical composition that solved the above problems comprising of one or more stabilizer compounds selected from the group consisting of magnesium oxide, calcium oxide, sodium carbonate, disodium hydrogen phosphate, sodium citrate, dipotassium hydrogen phosphate, sodium acetate, sodium hydrogen carbonate, and sodium hydroxide.

US Publication No. 20130296365A1 discloses that when alkaline earth metal carbonate is used in combination with a disintegrant the pharmaceutical composition of lenvatinib mesylate that is excellent in dissolution, is stable even after a long term storage.

PCT Publication No. WO2017028660 discloses a pharmaceutical composition comprising lenvatinib or pharmaceutically acceptable salt thereof, and a basic substance, the basic substance is selected from one or more of the following substances: 1) basic amino acids, 2) meglumine, 3) potassium carbonate wherein the composition is free of microcrystalline cellulose.

PCT Publication No. WO2018185175A1 discloses the pharmaceutical composition comprising a therapeutically effective dose of lenvatinib mesylate and sodium carbonates, wherein the weight ratio of lenvatinib mesylate to sodium carbonate ranges from 1:1.5 to 1:5.

However, there still exists a need to develop pharmaceutical composition of lenvatinib mesylate which overcomes the problems of gelation and degradation that is bioequivalent to commercial lenvatinib mesylate capsules (Lenvima®).

OBJECTS OF THE INVENTION

In one object, the present invention provides herein, pharmaceutical composition of capsule consisting essentially of a therapeutically effective amount of lenvatinib mesylate and an excipient that facilitates oral administration.

In another objective, the present invention provides pharmaceutical composition of capsule which is comprising lenvatinib mesylate, diluent, binder, stabilizer, disintegrating agent and lubricant.

SUMMARY OF THE INVENTION

The present invention relates to a pharmaceutical composition comprising lenvatinib mesylate and a stabilizer in an amount of about 10% to about 20% based on the total weight of the composition.

The present invention further relates to a pharmaceutical composition comprising lenvatinib mesylate and a stabilizer in an amount of about 10% to about 20% based on the total weight of the composition, wherein the stabilizer is selected from the group consisting of calcium hydroxide and potassium hydroxide.

The present invention also relates to a pharmaceutical composition comprising
a) lenvatinib mesylate in an amount of about 4% to about 15% by weight;
b) calcium hydroxide in an amount of about 10% to about 15% by weight;
c) potassium hydroxide in an amount of about 1% to about 5% by weight;
d) microcrystalline cellulose in an amount of about 15% to about 25% by weight;
e) mannitol in an amount of about 20% to about 35% by weight;
f) low-substituted hydroxypropyl cellulose in an amount of about 20% to about 30% by weight;
g) hydroxypropyl cellulose in an amount of about 1% to about 5% by weight; and
h) talc in an amount of about 1% to about 5% by weight.

DETAILED DESCRIPTION OF THE INVENTION

The present invention provides pharmaceutical composition of capsule consisting essentially of a therapeutically effective amount of lenvatinib mesylate and an excipient that facilitates oral administration.

In a preferred embodiment, the pharmaceutical composition of the invention is capsule.

In a most preferred embodiment, the pharmaceutical capsule composition comprises lenvatinib mesylate and pharmaceutically acceptable excipients.

Lenvatinib mesylate is preferably used in the pharmaceutical composition in an amount of about 4% to about 15% based on the total weight of the composition. The pharmaceutical capsule composition contains most preferably lenvatinib mesylate in an amount of about 4.9% (equivalent to 4% lenvatinib base) and in an amount of 12.25% (equivalent to 10% lenvatinib base) based on the total weight of the capsule composition.

In embodiments of the invention, the present invention provides a pharmaceutical composition comprising lenvatinib mesylate and a stabilizer.

Examples of the stabilizer used in the present invention are selected from the group consisting of potassium hydroxide and calcium hydroxide. Stabilizer preferred used in the pharmaceutical capsule composition of the present invention is preferably of about 1% to about 20% based on the total weight of the composition, more preferably of about 5% to about 20% based on the total weight of the composition and even more preferably of about 10% to about 20% based on the total composition and most preferably of about 10% to about 15% based on the total weight of the composition. Calcium hydroxide is used as a stabilizer more preferably in an amount of about 10% to about 15% based on the total weight of composition and most preferably in an amount of about 11% based on the total weight of the composition. Potassium hydroxide is used as a stabilizer more preferably in an amount of about 1% to about 5% based on the total weight of composition and most preferably in an amount of about 3% based on the total weight of the composition.

In embodiments of the invention, the present invention provides a pharmaceutical composition comprising lenvatinib mesylate and a stabilizer in an amount of about 10% to about 20% based on the total weight of the composition.

In embodiments of the invention, the present invention provides a pharmaceutical composition comprising lenvatinib mesylate, calcium hydroxide and potassium hydroxide.

In another embodiment of the invention, the present invention provides a pharmaceutical composition comprising of about 4% to about 15% by weight lenvatinib mesylate, about 10% to about 15% by weight calcium hydroxide and about 1% to about 5% by weight potassium hydroxide.

In further embodiments of the invention, the present invention provides a pharmaceutical composition comprising lenvatinib mesylate and a stabilizer in an amount of about 10% to about 20% based on the total weight of the composition, wherein the stabilizer is selected from group consisting of calcium hydroxide and potassium hydroxide.

In another embodiment, the pharmaceutical composition comprises lenvatinib mesylate, stabilizer selected from the group consisting of calcium hydroxide and potassium hydroxide, diluent, binder, disintegrating agent and a lubricant.

Examples of the diluent is selected from the group consisting of lactose, sucrose, glucose, cornstarch, mannitol, sorbitol, starch, microcrystalline cellulose, alpha starch, dextrin, crystalline cellulose, light anhydrous silicic acid, aluminum silicate, calcium silicate, magnesium aluminometasilicate, calcium hydrogen phosphate and including any mixtures thereof. Diluent preferably used in the pharmaceutical composition is of about 20% to about 80% based on the total weight of the composition. More preferably, the diluent used in the composition is in an amount of about 40% to about 70% based on total weight of the composition; and most preferably, the diluent used in the composition is in an amount of about 30% to about 60% based on total weight of the composition. Preferably, the diluents are selected from microcrystalline cellulose and mannitol. Microcrystalline cellulose is used in the composition in an amount of about 15% to about 25% based on total weight of the composition. Mannitol is used in the composition in an amount of about 20% to about 35% based on total weight of the composition.

Examples of the binder is selected from the group consisting of polyvinyl alcohol, methylcellulose, ethyl cellulose, gum Arabic, tragacanth, gelatin, shellac, hydroxypropylmethylcellulose, hydroxypropylcellulose, sodium carboxymethyl cellulose, polyvinylpyrrolidone and including any mixtures thereof. Preferably, the binder is selected from hydroxypropyl cellulose and hydroxypropyl cellulose used in the composition has a molecular weight of 80,000 and viscosity of about 300 to about 600 cps at 10% concentration in water by weight % as determined at 25° C. using Brookfield viscometer. Binder preferably used in composition is in an amount of about 1% to about 6% based on the total weight of composition. Most preferably, the binder is used in the composition is in an amount of about 1% to about 5% based on total weight of composition. Preferably hydroxypropyl cellulose used in the composition is in an amount of about 1% to about 5% based on the total weight of the composition, and most preferably in an amount of about 3% based on the total weight of the composition.

Examples of the disintegrating agent is selected from the group consisting of crystalline cellulose, agar, gelatin, calcium carbonate, sodium hydrogen carbonate, calcium citrate, dextrin, pectin, low-substituted hydroxypropyl cellulose, carboxymethylcellulose, carboxymethylcellulose calcium, croscarmellose sodium, carboxymethyl starch, carboxymethyl starch sodium, carmellose, carmellose sodium, crospovidone, low-substituted carboxymethyl starch sodium, partially alpha starch. Preferably, the disintegrating agent is selected from low-substituted hydroxypropyl cellulose. Low-substituted hydroxypropyl cellulose as used herein is preferably low substituted O-(2-hydroxypropylated) cellulose containing NLT 5.0% and NMT 16.0% of hydroxypropoxy groups (—OCH$_2$CHOHCH$_3$) calculated on the dried basis. Disintegrating agent preferably used in the pharmaceutical capsule composition is in an amount of about 10% to about 35% based on the total weight of blend composition. More preferably, the disintegrating agent used in the composition is in an amount of about 10% to about 30% based on the total weight of the composition and most preferably in an amount of about 20% to about 30% based on total weight of the composition. Preferably low-substituted hydroxypropyl cellulose used in the composition is in amount of about 10% to about 30% based on the total weight of the composition, even more preferably in an amount of about 20% to about 30% based on total weight of the composition and most preferably in an amount of about 25% on total weight of the composition. In preferred embodiments low-substituted hydroxypropyl cellulose is used in both the extragranular and intragranular portions of the composition, more preferably about 40% low-substituted hydroxypropyl cellulose based on total weight of low-substituted hydroxypropylcellulose is used in intragranular portion, and about 60% low-substituted hydroxypropyl cellulose based on total weight of low-substituted hydroxypropyl cellulose is used in extragranular portion.

Examples of the lubricant is selected from the group consisting of magnesium stearate, calcium stearate, sodium stearyl fumarate, talc, polyethylene glycol and colloidal silica. Preferably, the lubricant used is selected from talc. Lubricant preferably used in the pharmaceutical composition is in an amount of about 1% to about 5% based on the total weight of composition. Most preferably, the lubricant agent is used in an amount of about 2% based on the total weight of the composition.

In embodiments of the invention, the present invention relates to a pharmaceutical composition comprising
a) lenvatinib mesylate;
b) stabilizer selected from the group consisting of calcium hydroxide and potassium hydroxide;
c) at least one diluent in an amount of about 30% to about 60% based on the total weight of the composition;
d) at least one binder in an amount of about 1% to about 5% based on the total weight of the composition;
e) at least one disintegrating agent in an amount of about 10% to about 30% based on the total weight of composition; and
f) lubricant in an amount of about 1% to about 5% based on the total weight of the composition.

In further embodiments of the invention, the present invention relates to a pharmaceutical composition comprising
a) lenvatinib mesylate in an amount of about 4% to about 15% by weight;
b) stabilizer in an amount 10% to about 20% by weight, wherein stabilizer is selected from the group consisting of calcium hydroxide and potassium hydroxide;
c) at least one diluent in an amount of about 30% to about 60% based on the total weight of the composition;
d) at least one binder in an amount of about 1% to about 5% based on the total weight of the composition;
e) at least one disintegrating agent in an amount of about 10% to about 30% based on the total weight of composition; and
f) lubricant in an amount of about 1% to about 5% based on the total weight of the composition.

In embodiments of the invention, the present invention relates to a pharmaceutical composition comprising
a) lenvatinib mesylate in an amount of about 4% to about 15% by weight;
b) calcium hydroxide in an amount of about 10% to about 15% by weight;
c) potassium hydroxide in an amount of about 1% to about 5% by weight;
d) microcrystalline cellulose in an amount of about 15% to about 25% by weight;
e) mannitol in an amount of about 20% to about 35% by weight;
f) low-substituted hydroxypropyl cellulose in an amount of about 20% to about 30% by weight;
g) hydroxypropyl cellulose in an amount of about 1% to about 5% by weight; and
h) talc in an amount of about 1% to about 5% by weight.

In embodiments of the invention, the present invention relates to a pharmaceutical composition comprising
a) lenvatinib mesylate in an amount of about 4% to about 15% by weight;
b) calcium hydroxide in an amount of about 10% to about 15% by weight;
c) potassium hydroxide in an amount of about 1% to about 5% by weight;
d) microcrystalline cellulose in an amount of about 15% to about 25% by weight;
e) mannitol in an amount of about 20% to about 35% by weight;
f) low-substituted hydroxypropyl cellulose in an amount of about 20% to about 30% by weight;
g) hydroxypropyl cellulose in an amount of about 1% to about 5% by weight; and
h) talc in an amount of about 1% to about 5% by weight;
wherein the composition comprises of about 40% low-substituted hydroxypropyl cellulose based on total weight of low-substituted hydroxypropylcellulose as intragranular, and about 60% low-substituted hydroxypropyl cellulose based on total weight of low-substituted hydroxypropyl cellulose with whole amount of talc as extragranular.

In embodiments of the invention, the present invention relates to a pharmaceutical composition prepared by a process of wet granulation comprising the steps of
i) mixing lenvatinib mesylate, mannitol, microcrystalline cellulose, calcium hydroxide and of about 40% of low-substituted hydroxypropyl cellulose based on total weight of low-substituted hydroxypropyl cellulose in the composition to form a mixture;
ii) wet granulating the resultant mixture with solution comprising hydroxypropyl cellulose and potassium hydroxide dissolved in purified water to form an intragranular portion;
iii) further mixing the obtained intragranular portion with about 60% of low-substituted hydroxypropyl cellulose based on total weight of low-substituted hydroxypropyl cellulose in the composition and whole amount of talc to form granules; and
iv) optionally encapsulating the granules.

In specific embodiments of the invention, the present invention relates to a pharmaceutical composition prepared by a process of wet granulation comprising the steps of
i) mixing of about 4% to about 15% by weight of lenvatinib mesylate, about 20% to about 25% by weight of mannitol, about 15% to about 25% by weight microcrystalline cellulose, about 10% to about 15% by weight of calcium hydroxide and about 8% to about 12% of low-substituted hydroxypropyl cellulose in the composition to form a mixture;
ii) wet granulating the resultant mixture with solution comprising of about 1% to about 5% by weight of hydroxypropyl cellulose and about 1% to about 5% of potassium hydroxide dissolved in purified water to form an intragranular portion;

iii) further mixing the obtained intragranular portion with about 10% to about 20% of low-substituted hydroxypropyl cellulose and about 1% to about 5% of talc to form granules; and
iv) optionally encapsulating the granules.

In embodiments of the invention the dosage form is in the form of capsules or tablets and more specifically as capsules.

In embodiments of the invention, lenvatinib mesylate composition is used for the treatment of thyroid cancer, renal cell carcinoma and hepato cellular carcinoma.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example 1

Capsule with following compositions are prepared

| S. No | Ingredient | 4 mg Capsule (% w/w) | 10 mg Capsule (% w/w) |
|---|---|---|---|
| 1. | Lenvatinib mesylate | 4.9% | 12.25% |
| 2. | Microcrystalline cellulose | 10%-40% | 10%-40% |
| 3. | Mannitol | 10%-40% | 10%-40% |
| 4. | Hydroxy propyl cellulose | 1%-6% | 1%-6% |
| 5. | Potassium hydroxide | 1%-20% | 1%-20% |
| 6. | Hydroxy propyl cellulose (low-substituted) | 10%-35% | 10%-35% |
| 7. | Talc | 1%-6% | 1%-6% |
| | Total weight | 100% | 100% |

These pharmaceutical composition of capsule is prepared as follows: manufacturing process using wet granulation method:
1. Co-Sift weighed quantity of lenvatinib mesylate, microcrystalline Cellulose, mannitol, and low-substituted Hydroxypropyl cellulose through sieve #40.
2. Dry mix the above sifted blend in RMG/FBP for 10 minutes.
3. Prepare a binder solution by dissolving the hydroxypropyl cellulose in 80% of the purified water.
4. Granulate the material of step 2 using step 3 in RMG/FBP.
5. Dissolve potassium hydroxide in the remaining 20% of water, cool to room temperature and is sprayed onto the wet granules of step 4 until desired granules are obtained.
6. Dry the granules until the desired LOD is obtained.
7. Sift the contents of step 6 through sieve #20.
8. Sift weighed quantity of Talc and pass through sieve #60.
9. Load the contents of step 7 and step 8 into blender and blend for up to 15 min.
10. Fill the lubricated blend into the Hard Hypromellose capsules according to the fill weight.
11. Pack the capsules into polyamide/aluminium/PVC using Blister packing machine (as per requirement).

Example 2

Capsule with following compositions are prepared

| S. No | Ingredient | 4 mg Capsule (% w/w) | 10 mg Capsule (% w/w) |
|---|---|---|---|
| 1 | Lenvatinib mesylate | 4.9% | 12.25% |
| 2 | Microcrystalline cellulose | 10%-40% | 10%-40% |
| 3 | Mannitol | 10%-40% | 10%-40% |
| 4 | Hydroxy propyl cellulose | 1%-6% | 1%-6% |
| 5 | Calcium hydroxide | 1%-20% | 1%-20% |
| 6 | Hydroxy propyl cellulose (low-substituted) | 10%-35% | 10%-35% |
| 7 | Talc | 1%-6% | 1%-6% |
| | Total fill weight | 100% | 100% |

These pharmaceutical composition of capsule is prepared as follows: manufacturing process using wet granulation method:
1. Co-Sift weighed quantity of lenvatinib mesylate, microcrystalline cellulose, mannitol, calcium hydroxide and low substituted hydroxypropyl cellulose through sieve #40.
2. Dry mix the above sifted blend in RMG/FBP for 10 minutes.
3. Prepare a binder solution by dissolving the hydroxypropyl cellulose in purified water until a clear solution is obtained.
4. Granulate the material of step 2 using step 3 in RMG/FBP until desired granules are formed.
5. Dry the granules until the desired LOD is obtained.
6. Sift the contents of step 5 through sieve #20.
7. Sift weighed quantity of Talc and pass through sieve #60.
8. Load the contents of step 6 and step 7 into blender and blend for up to 15 minutes.
9. Fill the lubricated blend into the hard hypromellose capsules according to the fill weight.
10. Pack the capsules into polyamide/aluminium/PVC using Blister packing machine (as per requirement).

Example: 3

Capsules with following pharmaceutical composition are prepared

| | | 4 mg capsule | | 10 mg capsule | |
|---|---|---|---|---|---|
| S. No | Ingredients | mg/cap | % w/w | mg/cap | % w/w |
| 1. | Lenvatinib mesylate | 4.9 | 4.9 | 12.25 | 12.25 |
| 2. | Microcrystalline cellulose | 30.0 | 30.0 | 30.0 | 30.0 |
| 3. | Mannitol | 29.1 | 29.1 | 21.75 | 21.75 |
| 4. | Hydroxy propyl cellulose | 3.0 | 3.0 | 3.0 | 3.0 |
| 5. | Potassium hydroxide | 5.0 | 5.0 | 5.0 | 5.0 |
| 6. | Hydroxy propyl cellulose (low-substituted) | 25.0 | 25.0 | 25.0 | 25.0 |
| 7. | Talc | 3.0 | 3.0 | 3.0 | 3.0 |
| | Total | 100 | 100 | 100 | 100 |

Process for Preparation:

These pharmaceutical composition of capsule is prepared as follows: manufacturing process using wet granulation method:
1. Co-Sift weighed quantity of lenvatinib mesylate, microcrystalline Cellulose, mannitol, and low-substituted Hydroxypropyl cellulose through sieve #40.
2. Dry mix the above sifted blend in RMG/FBP for 10 minutes.
3. Prepare a binder solution by dissolving the hydroxypropyl cellulose and potassium hydroxide in purified water.
4. Granulate the material of step 2 using step 3 in RMG/FBP.
5. Dry the granules until the desired LOD is obtained.
6. Sift the contents of step 5 through sieve #20.
7. Sift weighed quantity of Talc and pass through sieve #60.
8. Load the contents of step 6 and step 7 into blender and blend for up to 15 min.
9. Fill the lubricated blend into the Hard Hypromellose capsules according to the fill weight.
10. Pack the capsules into polyamide/aluminium/PVC using Blister packing machine (as per requirement).

Example: 4

Capsules with following pharmaceutical composition are prepared

|       |                           | 4 mg capsule | | 10 mg capsule | |
|-------|---------------------------|--------------|--------|---------------|--------|
| S. No | Ingredients               | mg/cap | % w/w | mg/cap | % w/w |
| 1.    | Lenvatinib mesylate       | 4.9    | 4.9   | 12.25  | 12.25 |
| 2.    | Microcrystalline cellulose| 20.0   | 20.0  | 20.0   | 20.0  |
| 3.    | Mannitol                  | 30.1   | 30.1  | 22.75  | 22.75 |
| 4.    | Hydroxy propyl cellulose  | 3.0    | 3.0   | 3.0    | 3.0   |
| 5.    | Calcium hydroxide         | 14.0   | 14.0  | 14.0   | 14.0  |
| 6.    | Hydroxy propyl cellulose (low-substituted) | 25.0 | 25.0 | 25.0 | 25.0 |
| 7.    | Talc                      | 3.0    | 3.0   | 3.0    | 3.0   |
|       | Total                     | 100    | 100   | 100    | 100   |

Process for Preparation:

These pharmaceutical composition of capsule is prepared as follows: manufacturing process using wet granulation method:
1. Co-Sift weighed quantity of lenvatinib mesylate, microcrystalline cellulose, mannitol, calcium hydroxide and low substituted hydroxypropyl cellulose through sieve #40.
2. Dry mix the above sifted blend in RMG/FBP for 10 minutes.
3. Prepare a binder solution by dissolving the hydroxypropyl cellulose in purified water until a clear solution is obtained.
4. Granulate the material of step 2 using step 3 in RMG/FBP until desired granules are formed.
5. Dry the granules until the desired LOD is obtained.
6. Sift the contents of step 5 through sieve #20.
7. Sift weighed quantity of Talc and pass through sieve #60.
8. Load the contents of step 6 and step 7 into blender and blend for up to 15 minutes.
9. Fill the lubricated blend into the hard hypromellose capsules according to the fill weight.
10. Pack the capsules into polyamide/aluminium/PVC using Blister packing machine (as per requirement).

Example 5: Stability Studies

The compositions of example 3 and 4 are stored at 40° C./75% RH and was tested for impurities at specific intervals. The results of examples 3 and 4 are tabulated in tables 1 and 2 respectively.

TABLE 1

(Example 3) 10 mg Capsule

| Time | Assay | Imp-1 | Imp-2 | Imp-3 | Imp-4 | Imp-5 | Single Major unknown Imp | Total Impurity |
|------|-------|-------|-------|-------|-------|-------|--------------------------|----------------|
| Initial | 99.0 | 0.047 | 0.086 | ND | 0.047 | ND | 0.077 | 0.478 |
| 1 M  | 98.0  | 0.011 | 0.078 | 0.036 | 0.054 | ND | 0.1 | 0.637 |
| 2 M  | 99.0  | ND    | 0.081 | 0.010 | 0.050 | 0.033 | 0.156 | 0.789 |

TABLE 2

(Example 4) 10 mg Capsule

| Time | Assay | Imp-1 | Imp-2 | Imp-3 | Imp-4 | Imp-5 | Single Major unknown Imp | Total Impurity |
|------|-------|-------|-------|-------|-------|-------|--------------------------|----------------|
| Initial | 95.5 | 0.02  | 0.053 | ND | 0.03 | ND | 0.07 | 0.239 |
| 1 M  | 99.0  | 0.009 | 0.071 | ND | 0.046 | ND | 0.060 | 0.390 |
| 2 M  | 98.2  | ND    | 0.081 | ND | 0.050 | ND | 0.072 | 0.488 |

Example 6: Dissolution Studies

Dissolution studies of compositions of example 3 and 4 are conducted in 900 mL 0.1N HCl media with USP Apparatus II (Paddle) and release of lenvatinib mesylate at time points of 5, 10, 15, 20 & 30 months on stability at 40° C./75% RH are as follows in Table-3.

TABLE 3

(Example 3) - 10 mg Capsule

| Time Points | % Drug Release Initial | % Drug Release 1 M 40° C./75% RH | % Drug Release 2 M 40° C./75% RH |
|---|---|---|---|
| 5 | 1.0 | 8.2 | 10.0 |
| 10 | 34.9 | 38.3 | 29.0 |
| 15 | 60.7 | 66.2 | 45.0 |
| 20 | 77.8 | 79.0 | 58.0 |
| 30 | 92.1 | 90.0 | 87.0 |

TABLE 4

(Example 4) - 10 mg Capsule

| Time Points | % Drug Release Initial | % Drug Release 1 M 40° C./75% RH | % Drug Release 2 M 40° C./75% RH |
|---|---|---|---|
| 5 | 13.4 | 1.5 | 29.4 |
| 10 | 54.9 | 51.7 | 68.2 |
| 15 | 79 | 70.3 | 90.4 |
| 20 | 86.7 | 75.3 | 99.0 |
| 30 | 95.6 | 92.3 | 100.4 |

Example 7

Capsules with following pharmaceutical composition are prepared

| | | 4 mg capsule | | 10 mg capsule | |
|---|---|---|---|---|---|
| S. No | Ingredients | mg/cap | % w/w | mg/cap | % w/w |
| | Intra-granular Portion | | | | |
| 1. | Lenvatinib mesylate | 4.9 | 4.9 | 12.26 | 12.25 |
| 2. | Microcrystalline cellulose | 20 | 20.0 | 20.0 | 20.0 |
| 3. | Mannitol | 31.1 | 31.1 | 23.74 | 23.74 |
| 4. | Hydroxy propyl cellulose (low-substituted) | 10.0 | 10.0 | 10.0 | 10.0 |
| 5. | Calcium hydroxide | 11.0 | 11.0 | 11.0 | 11.0 |
| | Binder | | | | |
| 6. | Hydroxy propyl cellulose | 3.0 | 3.0 | 3.0 | 3.0 |
| 7. | Potassium hydroxide | 3.0 | 3.0 | 3.0 | 3.0 |
| | Extra-granular Portion | | | | |
| 8. | Hydroxy propyl cellulose (low-substituted) | 15.0 | 15.0 | 15.0 | 15.0 |
| 9. | Talc | 2.0 | 2.0 | 2.0 | 2.0 |
| | Total | 100 | 100 | 100 | 100 |

Process for Preparation:

These pharmaceutical composition of capsule is prepared as follows: manufacturing process using wet granulation method:

1. Co-Sift weighed quantity of lenvatinib mesylate, microcrystalline cellulose, mannitol, calcium hydroxide and low substituted hydroxypropyl cellulose through sieve #30.
2. Dry mix the above sifted blend in RMG/FBP for 10 minutes.
3. Prepare a binder solution by dissolving the hydroxypropyl cellulose and potassium hydroxide in purified water until a clear solution is obtained.
4. Granulate the material of step 2 using step 3 in RMG/FBP until desired granules are formed.
5. Dry the granules until the desired LOD is obtained.
6. Sift the contents of step 5 through sieve #20.
7. Sift weighed quantity of low-substituted hydroxypropyl cellulose through sieve #30 and talc and pass through sieve #40.
8. Load the contents of step 6 and step 7 into blender and blend for up to 15 minutes.
9. Fill the lubricated blend into the hard hypromellose capsules according to the fill weight.
10. Pack the capsules into polyamide/aluminium/PVC using Blister packing machine (as per requirement).

Example 8: Stability Studies

The compositions of example 7 are stored at 40° C./75% RH and was tested for impurities at specific intervals. The results of examples 7 are tabulated in tables 5 and 6.

TABLE 5

(Example 7) 4 mg Capsule

| Time | Assay | Imp-1 | Imp-2 | Imp-3 | Imp-4 | Imp-5 | Single Major unknown Imp | Total Impurity |
|---|---|---|---|---|---|---|---|---|
| Initial | 100.1 | ND | ND | ND | 0.072 | ND | 0.022 | 0.009 |
| 1 M | 102.6 | ND | ND | ND | 0.072 | ND | 0.040 | 0.04 |
| 3 M | 101.1 | ND | 0.023 | ND | 0.072 | ND | 0.055 | 0.06 |
| 6 M | 102.2 | ND | 0.059 | 0.019 | 0.072 | ND | 0.078 | 0.15 |

TABLE 6

| | (Example 7) 10 mg Capsule | | | | | | |
|---|---|---|---|---|---|---|---|
| Time | Assay | Imp-1 | Imp-2 | Imp-3 | Imp-4 | Imp-5 | Single Major unknown Imp | Total Impurity |
| Initial | 100.3 | ND | ND | ND | 0.072 | ND | 0.022 | 0.009 |
| 1 M | 98.7 | ND | ND | ND | 0.072 | ND | 0.026 | 0.03 |
| 3 M | 99.3 | ND | 0.023 | 0.019 | 0.072 | ND | 0.031 | 0.03 |
| 6 M | 101.8 | ND | 0.023 | 0.019 | ND | ND | 0.04 | 0.04 |

Example 9: Dissolution Studies

Dissolution studies of compositions of example 7 are conducted in 900 mL 0.1N HCl media with USP Apparatus II (Paddle) and release of lenvatinib mesylate at time points of 5, 10, 15, 20 & 30 minutes on stability at 40° C./75% RH are as follows in Table 8 & 9.

TABLE 8

| | (Example 7) - 4 mg Capsule | | | | |
|---|---|---|---|---|---|
| Time Points | % Drug Release Initial | % Drug Release 1 M 40° C./75% RH | % Drug Release 2 M 40° C./75% RH | % Drug Release 3 M 40° C./75% RH | % Drug Release 6 M 40° C./75% RH |
| 5 | 23 | 23.7 | 11.0 | 21 | 24.6 |
| 10 | 68 | 77.9 | 70.0 | 87 | 78.4 |
| 15 | 90 | 92.2 | 89.0 | 100 | 96.8 |
| 20 | 98 | 101.0 | 97.0 | 102 | 100.5 |
| 30 | 99 | 102.6 | 99.0 | 102 | 100.5 |

TABLE 9

| | (Example 7) - 10 mg Capsule | | | | |
|---|---|---|---|---|---|
| Time Points | % Drug Release Initial | % Drug Release 1 M 40° C./75% RH | % Drug Release 2 M 40° C./75% RH | % Drug Release 3 M 40° C./75% RH | % Drug Release 6 M 40° C./75% RH |
| 5 | 6 | 26.7 | 26.0 | 19.9 | 24.9 |
| 10 | 56 | 75.9 | 73.0 | 62.6 | 82.0 |
| 15 | 79 | 94.9 | 89.0 | 85.0 | 91.0 |
| 20 | 90 | 99.4 | 94.0 | 93.8 | 95.1 |
| 30 | 98 | 102.6 | 97.0 | 97.4 | 97.7 |

Example 10: Bioequivalence Studies of Example 7 (10 mg Capsule) with Reference to Lenvima® 10 mg Capsule Two studies fed and fasting Bioequivalence study of Lenvatinib mesylate 10 mg capsules of example 7 was conducted with reference to Lenvima® 10 mg Capsules.

Figure 1:
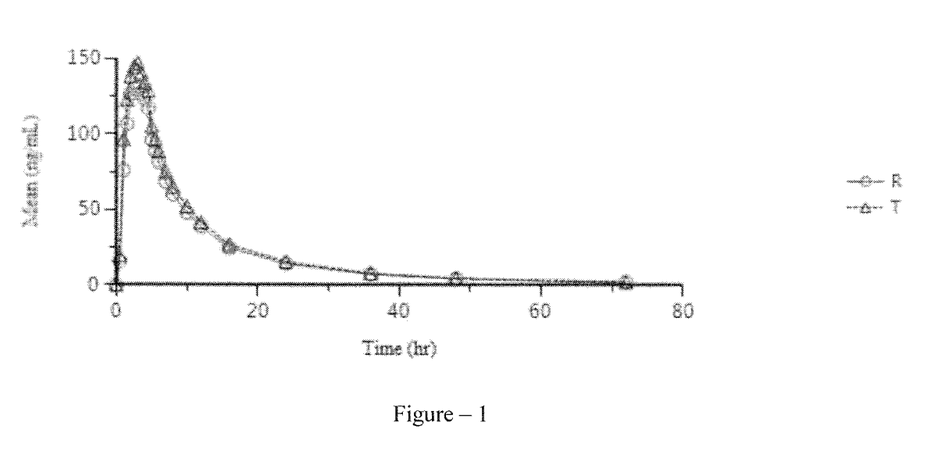
FIG. 1 discloses the fasting study linear plot of mean plasma concentration vs. time of test (T) example-7 (10 mg Capsule) and reference (R) formulation.
Figure 2:
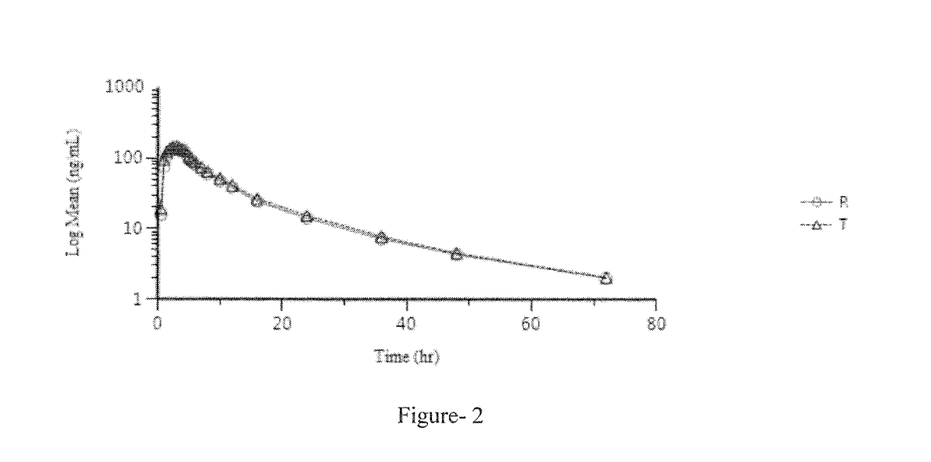
FIG. 2 discloses the fasting study semi-log plot of mean plasm concentration vs. time of test (T) example-7 (10 mg Capsule) and reference (R) formulation.

Fasting Bio-Equivalence Study:

An open label, balanced, randomized, two treatments, two period, two sequence, single dose, crossover, oral bioequivalence study in sixty healthy, adult, human subjects under fasting conditions. Lenvatinib 10 mg capsule (1 Capsule) of example 7 (test formulation) was administered with reference to Lenvima® 10 mg capsule (1 Capsule). The results of fasting study of the inventive formulation (example 7 test formulation) and reference (Lenvima) capsules are depicted in Table-10. The linear plot of mean plasma concentration vs. time and semi-log plot of mean plasm concentration vs. time of fasting study [test (T) and reference (R) formulation] are disclosed in FIG. 1 and FIG. 2 respectively.

TABLE 10

| Parameter | 90% confidence interval | | T/R Ratio (%) | Power (%) |
|---|---|---|---|---|
| Cmax (ng/ml) | 104.82 | 124.37 | 114.18 | 99.5 |
| $AUC_{0-t}$ | 106.3 | 116.97 | 111.36 | 100.0 |
| $AUC_{0-inf}$ | 105.68 | 116.12 | 110.78 | 100.0 |

Figure 3:
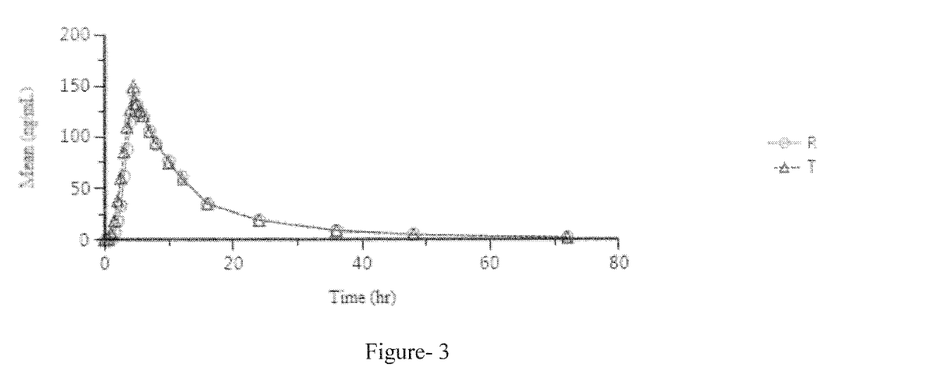
FIG. 3 discloses the fed study linear plot of mean plasma concentration vs. time of test (T) example-7 (10 mg Capsule) and reference (R) formulation.
Figure 4:
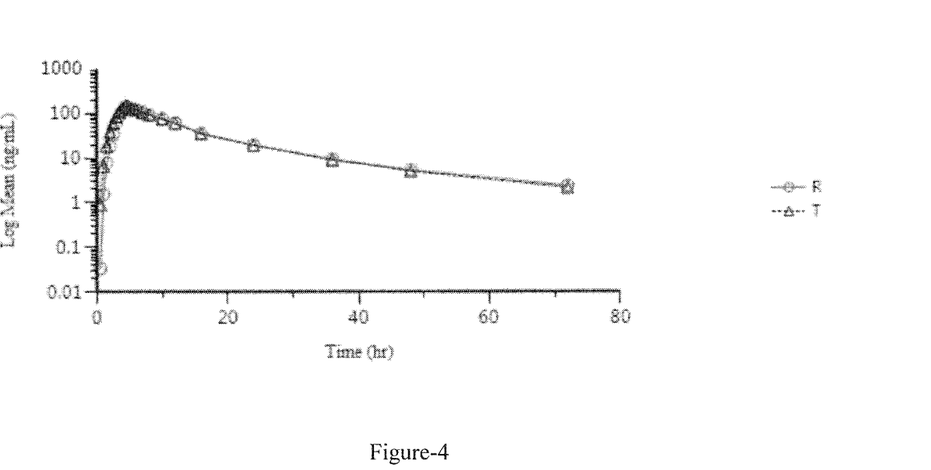
FIG. 4 discloses the fed study semi-log plot of mean plasm concentration vs. time of test (T) example-7 (10 mg Capsule) and reference (R) formulation.

Fed Bio-Equivalence Study:

An open label, balanced, randomized, two treatments, two period, two sequence, single dose, crossover, oral bioequivalence study in forty-eight healthy, adult, human subjects under fed conditions. Lenvatinib 10 mg capsule (1 Capsule) of example 7 (test formulation) was administered with reference to Lenvima® 10 mg capsule (1 Capsule). The results of fed study of the inventive formulation (example 7 test formulation) and reference (Lenvima) capsules are depicted in Table-11. The linear plot of mean plasma concentration vs. time and semi-log plot of mean plasm concentration vs. time of fed study [test (T) and reference (R) formulation] are disclosed in FIG. 3 and FIG. 4 respectively.

TABLE 11

| Parameter | 90% confidence interval | | T/R Ratio (%) | Power (%) |
|---|---|---|---|---|
| Cmax (ng/ml) | 99.97 | 112.28 | 105.94 | 100.0 |
| AUC$_{0-t}$ | 98.43 | 107.80 | 103.01 | 100.0 |
| AUC$_{0-inf}$ | 98.17 | 107.37 | 102.67 | 100.0 |

The invention claimed is:

1. A pharmaceutical composition comprising lenvatinib mesylate and a stabilizer in an amount of about 10% to about 20% based on the total weight of the composition, wherein the stabilizer is selected from the group consisting of calcium hydroxide and potassium hydroxide.

2. A pharmaceutical composition according to claim 1, wherein the composition further comprises
   a) at least one diluent in an amount of about 30% to about 60% based on the total weight of the composition;
   b) at least one binder in an amount of about 1% to about 5% based on the total weight of the composition;
   c) at least one disintegrating agent in an amount of about 10% to about 30% based on the total weight of composition; and
   d) lubricant in an amount of about 1% to about 5% based on the total weight of the composition.

3. A pharmaceutical composition according to claim 2, wherein diluent is selected from group consisting microcrystalline cellulose, mannitol, or mixtures thereof.

4. A pharmaceutical composition comprising lenvatinib mesylate, calcium hydroxide and potassium hydroxide.

5. A pharmaceutical composition according to claim 4, wherein the composition comprises calcium hydroxide in an amount of about 10% to about 15% based on the total weight of the composition.

6. A pharmaceutical composition accord claim 4, wherein the composition comprises potassium hydroxide in an amount about 1% to about 5% based on the total weight of the composition.

7. A pharmaceutical composition according to claim 4, wherein the composition further comprises
   a) microcrystalline cellulose in an amount of about 15% to about 25% by weight;
   b) mannitol in an amount of about 20% to about 35% by weight;
   c) low-substituted hydroxypropyl cellulose in an amount of about 20% to about 30% by weight;
   d) hydroxypropyl cellulose in an amount of about 1% to about 5% by weight; and
   e) talc in an amount of about 1% to about 5% by weight.

8. A pharmaceutical composition comprising
   a) lenvatinib mesylate in an amount of about 4% to about 15% by weight;
   b) calcium hydroxide in an amount of about 10% to about 15% by weight;
   c) potassium hydroxide in an amount of about 1% to about 5% by weight;
   d) microcrystalline cellulose in an amount of about 15% to about 25% by weight;
   e) mannitol in an amount of about 20% to about 35% by weight;
   f) low-substituted hydroxypropyl cellulose in an amount of about 20% to about 30% by weight;
   g) hydroxypropyl cellulose in an amount of about 1% to about 5% by weight; and
   h) talc in an amount of about 1% to about 5% by weight.

9. A pharmaceutical composition according to claim 8, wherein the composition comprises of about 40% low-substituted hydroxypropyl cellulose based on total weight of low-substituted hydroxypropylcellulose as intragranular, and about 60% low-substituted hydroxypropyl cellulose based on total weight of low-substituted hydroxypropyl cellulose with whole amount of talc as extragranular.

* * * * *